United States Patent [19]

Ueno et al.

[11] Patent Number: 5,169,863

[45] Date of Patent: Dec. 8, 1992

[54] HYPERSPHYXIA-CAUSING METHODS

[75] Inventors: Ryuzo Ueno; Ryuji Ueno, both of Nishinomiya; Tomio Oda, Sanda, all of Japan

[73] Assignee: K.K. Ueno Seiyaku Oyo Kenkyujo, Osaka, Japan

[21] Appl. No.: 672,758

[22] Filed: Mar. 22, 1991

Related U.S. Application Data

[63] Continuation of Ser. No. 355,526, May 23, 1989, abandoned.

[30] Foreign Application Priority Data

May 23, 1988 [JP] Japan .................. 63-125303
Jul. 20, 1988 [JP] Japan .................. 63-182281

[51] Int. Cl.$^5$ .................. A61K 31/35; A61K 31/215
[52] U.S. Cl. .................. 514/451; 514/530
[58] Field of Search .................. 514/530, 451

[56] References Cited

U.S. PATENT DOCUMENTS 4,447,428 5/1984 Collington et al. .......... 514/530 X

FOREIGN PATENT DOCUMENTS 30153858 9/1985 European Pat. Off. .

OTHER PUBLICATIONS

Chemical Abstracts, vol. 74, No. 23, Jun. 7, 1971, p. 78, Ref. No. 120819y.
Chemical Abstracts, vol. 76, No. 21, May 22, 1972, p. 75, Ref. No. 122009z.
Prostanglandins, vol. 4, No. 6, Dec. 1973, pp. 877-890, Mathe, et al.

*Primary Examiner*—Leonard Schenkman
*Attorney, Agent, or Firm*—Sughrue, Mion, Zinn, Macpeak & Seas

[57] ABSTRACT

This invention provides a hypersphyxia-causing composition containing 15-keto-PGEs esters separated from any substantial activity such as decrease of blood pressure.

The present invention provides a hypersphyxia-causing composition effective to recovery of blood pressure, and heart rate in e.g. hemmorrhage shock, or hyperventilation, which comprises 15-keto PGEs esters.

19 Claims, 2 Drawing Sheets

HYPERSPHYXIA-CAUSING METHODS

This is a continuation of application Ser. No. 07/355,526 filed May 23, 1989 abandoned.

BACKGROUND OF THE INVENTION

This invention relates to a hypersphyxia-causing composition containing 15-keto-prostaglandin E esters and their derivatives.

In the present specification the term "hypersphyxia-causing compositions" means a composition having an activity of progressing breath, increasing a heart rate, increasing blood pressure and the like.

15-keto-prostaglandin E (noted as 15-keto-PGE hereinafter) and 13,14-dihydro-15-keto-prostaglandin E (noted as 13,14-dihydro-15-keto-PGE hereinafter) are known as a substance naturally produced by an enzyme in the metabolism of prostaglandin E (noted as PGE hereinafter) in a living body. These 15-keto-PGE have been considered to be physiologically and pharmacologically inactive substances (Acta Physiologica Scandinavica, Vol. 66, pp509 (1966)). It has never been recognized that these 15-keto-PGE have hypersphyxia activity.

SUMMARY OF THE INVENTION

It has been found that 15-keto-PGEs esters have an activity of increasing blood pressure, a heart rate, and a blood flow rate in, for instance, hemorrhage shock, and hyperventilation. Accordingly, the esters of 15-keto-PGEs are effective as a composition for hypersphyxia-causing methods for treating of a patient suffering from hypergasia of the circulation, wherein the methods comprise administering to the patient a pharmacologically effective amount of a 15-keto-PGE ester, and wherein the hypergasia can be hypertension, decrease in heart rate, decrease in blood flow, decrease in blood pressure, or decrease in circulation.

Especially useful 15-keto-PGEs esters for the hypersphyxia are compounds having one or two alkyl group(s), particularly methyl group(s) on 3-, 16- and/or 19-position or one or two halogen atom(s), particularly fluorine atom(s) on 16-position.

DETAILED DESCRIPTION OF THE INVENTION

This invention provides a hypersphyxia-causing composition which comprises 15-keto-PGEs esters as an active ingredient.

In this invention, 15-keto-PGEs esters include esters of 15-keto-PGEs of which the carbon atom of 15-position constitutes a carbonyl group, and 13,14-dihydro-15-keto-PGEs of which the bond between carbon atoms of 13- and 14-position is saturated and the carbon atom of 15-position constitutes a carbonyl group. Therefore, this invention includes every prostaglandin E as long as it has in 15-keto or 13,14-dihydro-15-keto form in the prostaglandin skeleton structure and is not limited by other additional skeleton structure or substituents.

In the present specification 15-keto-PGEs are expressed according to the following nomenclature. The 15-keto-PGEs have a following basic structure:

and the position number of carbon atom constituting α-chain, ω-chain and five membered ring in the prostaglandin skeleton structure is used as it is in the drawing. That is, the position number of the carbon atom in the skeleton structure is started from the carbon atom constituting carboxylic acid of the terminal position of α-chain through the five membered ring to ω-chain, i.e. 1 to 7 are attached to the carbon atoms in the α-chain in this order, 8–12 are attached to the carbon atoms in the five membered ring, and 13–20 are attached to the carbon atoms in the ω-chain. In the compound whose carbon number in "-chain is less than 7 the position number is simply eliminated from 2 to 7 in this order without any change of the position number of the other carbons. In other word 15-keto-PGEs having 6 carbon atoms in the α-chain have no position of 2, i.e. 15-keto-PGEs of such compound are not renamed as 14-keto-PGEs. In case that carbon atoms increase in the α-chain the carbon chain increased is nominated as a substituent on the carbon of position number 2 without any change of the position number of the other carbons. Therefore, 15-keto-PGEs having 8 carbon atoms in the α-chain are nominated as 15-keto-2-decarboxy-2-acetic acid-PGEs. In case that the number of the carbon in the ω-chain decreases the position number is nominated as reducing it from the carbon of position number 20 one by one. In case the number of the carbon atoms in the ω-chain increases, the increased carbon chain is nominated as a substituent on the carbon of position number 20. That is, 15-keto-PGEs having 10 carbon atoms in the ω-chain is nominated as 15-keto-20-ethyl-PGEs.

The above formula expresses a specific configuration which is most typical one, and in this specification compounds having such a configuration are expressed unless otherwise described.

PGEs have a hydroxy group on the 11-position in general, but in the present specification term "PGEs" includes prostaglandins having another group instead of said hydroxyl group of normal PGE. Such PGEs are called as 11-dehydroxy-11-substituent-PGEs, for instance, 11-dehydroxy11-methyl-PGEs in case of the substituent being a methyl group.

PGEs are classified to $PGE_1$ and $PGE_2$ according to the bonds between 5- and 6-positions.

$PGE_1$ and its derivatives (referred to as $PGE_1$s hereinafter) are nominated to a group of compounds in which the bond between 5- and 6-positions is a single bond. $PGE_2$ and its derivatives (referred to as $PGE_2$s hereinafter) are called to a group of compounds in which the bond between 5- and 6-positions is a cis-double bond. PGEs having a structure of is nominated as 6-keto-PGE$_1$s, and PGEs having a structure of is called as 5,6-dehydro-PGE$_2$s.

The hypersphyxia-causing activity is remarkably expressed in 15-keto-PGEs esters represented by the following formula:

wherein R$_1$ is a hydroxyl group, a hydroxyalkyl group, or an alkyl group; Y is a saturated or unsaturated hydrocarbon moiety having 2-6 carbon atoms wherein a portion of carbon atoms constituting the hydrocarbon moiety may be carbonyl carbon or a portion of hydrogen atoms attached to the hydrocarbon moiety may be substituted with other atoms or groups; Z is a saturated or an unsaturated hydrocarbon moiety which may constitute a straight chain or a ring, wherein a portion of hydrogen atoms in the hydrocarbon moiety may be substituted with other atoms or groups; COOR$_2$ is a physiologically acceptable ester group.

Y represents a saturated or an unsaturated hydrocarbon moiety having 2-6 carbon atoms includes an aliphatic hydrocarbon such as an alkylene group, an alkenylene group, an alkynylene group and the like. Y may preferably be a hydrocarbon chain having 6 carbon atoms.

Examples of PGEs of which Y is an unsaturated hydrocarbon moiety are PGE$_2$s, 5,6-dehydro-PGE$_2$s, PGEs of which the bond between 2- and 3-positions is a double-bond, and the like.

A portion of carbon atoms constituting hydrocarbon moiety represented by Y may be a carbonyl group, whose typical examples are 6-keto-PGE$_1$s in which the carbon atom of 6-position is a carbonyl group.

The hydrocarbon moiety represented by Y may be substituted with one or more other atom(s) or group(s), for example, halogen atoms such as a fluorine atom, a chlorine atom, typically a fluorine atom; an alkyl group such as methyl, ethyl; a hydroxyl group and the like. Typical examples of such substituents are 15-keto-PGEs having one or more alkyl group(s) on the carbon atom of 3-position.

Z represents a saturated or an unsaturated hydrocarbon moiety having 1-10 carbon atoms. The hydrocarbon moiety may be an aliphatic hydrocarbon or a cyclic hydrocarbon itself or in part. The hydrocarbon moiety represented by Z may be substituted with one or more other atom(s) or group(s).

The number of the carbon atoms of Z is preferably 3-7 in straight chain. PGEs in which carbon numbers of Z are 5 are typical PGs. Therefore, the PGEs in which carbon numbers of the hydrocarbon moiety represented by Z are 6 or more than 6 are nominated as PGEs having a substituent on the carbon atom of 20-position. That is, PGEs in which the number of carbon atoms of Z is 6 are nominated as 20-methylPGEs.

Though the hydrocarbon moiety represented by Z may have one or more unsaturated bond(s) at any position, a saturated hydrocarbon is more preferable. Examples of the hydrocarbon moiety having a cycloalkyl group are a cyclopentyl or a cyclohexyl containing a carbon atom itself of 16- or 17-position as a ring constituting member.

The hydrocarbon moiety represented by Z may be substituted with one or more other atom(s) or group(s), for example, a halogen atom such as a fluorine atom or a chlorine atom; an alkyl group such as methyl, ethyl, isopropyl, isopropenyl; an alkoxy group such as methoxy, ethoxy; a hydroxyl group; a phenyl group; a phenoxy group and the like. The substituent(s) may be preferably located at the 16-, 17-, 19- and/or 20-position, but not restricted. Examples of preferable compounds include those having one or two, different or identical atom(s) and/or groups, for example, a halogen atom such as a fluorine atom; an alkyl group such as a methyl, an ethyl group; an aromatic group which may have substituents such as a methyl, ethyl, phenyl, benzyl, phenoxy, hydroxyl or other group on 16-position. Other examples of preferable compounds include those having a cycloalkyl group such as a cyclopentyl or cyclohexyl group which contains the carbon atom of 16-position as a constituent of the cyclic ring; an alkyl group such as methyl, ethyl and the like on 17- or 19-position; an alkyl group such as methyl, ethyl, isopropyl, isopropenyl and the like; an alkoxy group such as methoxy, ethoxy, propoxy and the like on 20-position.

A generic name of PGEs is used to compounds having a prostanoic acid structure in which the carbon atom of 11-position has a hydroxyl group, and the carbon atom of 9-position forms a carbonyl group. In the present specification prostaglandins derivatives in which the hydroxyl group on 11-position is substituted with a hydroxyalkyl group or an alkyl group is also called as PGEs. Therefore, the 15-keto-PGEs of the present invention include compounds in which R$_1$ of the general formula (I) represents a hydroxyalkyl group or an alkyl group, for example, as a hydroxyalkyl group hydroxymethyl, 1-hydroxyethyl, 2-hydroxyethyl and 1-methyl-1-hydroxyethyl groups; as an alkyl group methyl and ethyl groups are preferably exemplified.

The steric configuration of R$_1$ with respect to the carbon of 11-position may be α or β or mixture thereof.

Furthermore, examples of the PGEs included in the present invention are 13,14-dihydro compounds which have saturated bond between the 13- and 14-positions, and rather more preferable effects can be achieved from such 13,14dihydro compounds.

The 15-keto-PGEs of the present invention is esterified on the terminal carboxyl group.

Useful ester (COOR$_2$) of 15-keto-PGEs may include a saturated or an unsaturated lower alkyl ester which may have a branched chain such as methyl, ethyl, propyl, n-butyl, isopropyl, t-butyl, 2-ethylhexyl, allyl and the like; an aliphatic cyclic ester such as cyclopropyl, cyclopentyl, cyclohexyl and the like; an aromatic ester such as benzyl, phenyl and the like, which may have substituents; a hydroxyalkyl or an alkoxyalkyl ester such as hydroxyethyl, hydroxyisopropyl, hydroxypropyl, polyhydroxyethyl, polyhydroxyisopropyl, methoxyethyl, ethoxyethyl, methoxyisopropyl and the like; a trialkylsilyl ester such as trimethylsilyl, triethylsilyl and the like; a heterocyclic ester such as tetrahydropyranyl and the like. Preferable esters for the present invention are a lower alkyl ester which may have a branched chain, for instance, methyl, ethyl, propyl, n-butyl, isopropyl, t-butyl; a benzyl ester; a hydroxyalkyl ester such as hydroxyethyl, hydroxy isopropyl; and the like. In the alkyl ester remarkable results of hypersphyxia can be usually obtained.

15-keto-PGEs of the present invention may include various kinds of isomers such as tautomeric isomers, optical isomers, geometric isomers and the like. As an example of such isomers there is exemplified a ketohemiacetal tautomeric isomer between the hydroxyl group on 11-position and the carbonyl group of 15-position of 15-keto-PGEs. The latter tautomeric isomer is liable to be caused in 15-ketoPGEs having an electron withdrawing group such as fluorine atom on 16-position.

A hemiacetal, a tautomeric isomer between the hydroxyl group on 11-position and the carbonyl group of 15-position, may be sometimes formed, and an equilibrium mixture of the compound df $R_1$ being a hydroxyl group and a hemiacetal may be given. Such an equilibrium mixture or a tautomeric isomer is also included in the 15-keto-PGEs of the present invention.

An equilibrium mixture of the isomers such as racemic mixture, tautomers of a hydroxyl compound and a hemiacetal also exhibits similar effects to a single compound.

Examples of especially useful compounds for an accelerator of heart rate in hypersphyxia include compounds having one or two alkyl group(s), especially methyl group(s); halogen atom(s), especially fluorine atom(s) at 3-position, 16-position and/or 19-position; compounds in which $R_1$ is methyl; compounds in which the carbon number of the main chain of ω-chain is 8 to 10; the bond between 2- and 3- positions is double-bond.

The examples of 15-keto-PGEs especially effective to increase of heart rate are 13,14-dihydro-15-keto-$\Delta^2$-$PGE_1$ alkyl ester, 13,14-dihydro-15-keto-20-ethyl-$PGE_1$ alkyl ester, 13,14-dihydro-6,15-diketo-16,16-dimethyl-$PGE_1$ alkyl ester, 13,14-dihydro-6,15-diketo-16R,S-fluoro-$PGE_1$ alkyl ester, 13,14-dihydro-6,15-diketo-11-dehydroxy-11R-methyl$PGE_1$ alkyl eater, 13,14-dihydro-6,15-diketo-16R,S-fluoro-11-dehydroxy-11R-methyl-$PGE_1$ alkyl ester, 13,14-dihydro-15-keto-$PGE_2$ alkyl ester, 13,14-dihydro-15-keto-3R,S-methyl$PGE_2$ alkyl ester, 13,14-dihydro-15-keto-16R,S-methyl-$PGE_2$ alkyl ester, 13,14-dihydro-15-keto-3R,S,16R,S-dimethyl-$PGE_2$ alkyl ester, 13,14-dihydro-15-keto-16R,S-fluoro-$PGE_2$ alkyl ester, 13,14-dihydro-15-keto-16R,S-fluoro-20-methyl-$PGE_2$ alkyl ester, 13,14-dihydro-15-keto-19-methyl-$PGE_2$ alkyl ester, 13,14-dihydro-15-keto-20-methoxy-16,16-dimethyl-$PGE_2$ alkyl ester, 15-keto-16R,S-fluoro-$PGE_2$ alkyl ester.

Examples of 15-keto-PGEs especially useful for hypertension are compounds of $R_1$ being methyl; compounds of which the bond between 2- and 3-positions is a double bond; compounds in which possess one or two halogen atom(s) or alkyl group(s), especially fluorine atom(s) or methyl group(s) is bound on 16- and/or 19-position; compounds in which carbon number of main chain in the ω-chain is 8-12 etc.

Concrete examples of these preferable compounds are 13,14-dihydro-15-keto-$\Delta^2$-$PGE_1$ alkyl ester, 13,15-dihydro6,15-diketo-16,16-dimethyl-$PGE_1$ alkyl ester, 13,14-dihydro6,15-diketo-16R,S-methyl-$PGE_1$ alkyl ester, 13,14-dihydro6,15-diketo-16R,S-fluoro-$PGE_1$ alkyl ester, 13,14-dihydro6,15-diketo-11-dehydroxy-11R-methyl-$PGE_1$ alkyl ester, 13,14-dihydro-6,15-diketo-16R,S-fluoro-11-dehydroxy-11R-methyl$PGE_1$ alkyl ester, 13,14-dihydro-15-keto-$PGE_2$ alkyl ester, 13,14-dihydro-15-keto-16,16-dimethyl-$PGE_2$ alkyl ester, 13,14-dihydro-15-keto-16R,S-fluoro-11-dehydroxy-11R-methyl$PGE_2$ alkyl ester, 13,14-dihydro-15-keto-16R,S-hydroxy-$PGE_2$ alkyl ester, 13,14-dihydro-15-keto-16R,S-fluoro-$PGE_2$ alkyl ester, 13,14-dihydro-15-keto-16R,S-fluoro-20-methyl-$PGE_2$ alkyl ester, 13,14-dihydro-15-keto-11-dehydroxy-11R-methyl$PGE_2$ alkyl ester, 13,14-dihydro-15-keto-19-methyl-$PGE_2$ alkyl ester, 13,14-dihydro-15-keto-20-methoxy-16,16-dimentyl-$PGE_2$ alkyl ester, 13,14-dihydro-15-keto-20-ethyl-11-dehydroxy11R-methyl-$PGE_2$ alkyl ester, 13,14-dihydro-15-keto-20-n-propyl-$PGE_2$ alkyl ester and the like.

Examples of especially useful compounds for hyperventilation include compounds having one or two alkyl group(s), especially methyl; halogen atom(s), especially fluorine atom(s) at 3-position, 16-position and/or 19-position; compounds of which $R_1$ is methyl; and compounds of which the carbon number of the main chain of ω-chain is 8 to 10.

The examples of 15-keto-PGEs especially effective to increase of heart rate are 13,14-dihydro-15-keto-$PGE_1$ alkyl ester, 13,14-dihydro-15-keto-20-ethyl-$PGE_1$ alkyl ester, 13,14-dihydro-6,15-diketo-$PGE_1$ alkyl ester, 13,14-dihydro-6,15-diketo-16R,S-methyl $PGE_1$ alkyl ester, 13,14-dihydro-6,15-diketo-16,16-dimethyl-$PGE_1$ alkyl ester, 13,14-dihydro-6,15-diketo-16R,S-fluoro-$PGE_1$ alkyl ester, 13,14-dihydro-15-keto-3R,S-methyl-$PGE_2$ alkyl ester, 13,14-dihydro-15-keto-16R,S-methyl-$PGE_2$ alkyl ester, 13,14-dihydro-15-keto-3R,S,16R,S-dimethyl-$PGE_2$ alkyl ester, 13,14-dihydro-16,16-dimethyl-$PGE_2$ methyl ester, 13,14-dihydro-15-keto-20-ethyl-$PGE_2$ methyl ester, 13,14-dihydro-15-keto-16R,S-fluoro-$PGE_2$ alkyl ester, and 13,14-dihydro-15-keto-19-methyl-$PGE_2$ alkyl ester.

Examples of 15-keto-PGEs preferred in the aspect of heart rate, blood pressure increasing abilities and breath progressing activity are compounds having one or two alkyl group(s), especially methyl group(s) on 3-, 16- and/or 19- position or one or two halogen atom(s), especially fluorine atom(s) on 16-position.

Concrete examples of these preferable compounds are 13,14-dihydro-6,15-diketo-16-R,S-methyl-$PGE_1$ alkyl ester, 13,14-dihydro-6,15-diketo-16,16-dimethyl-$PGE_1$ alkyl ester, 13,14-dihydro-6,15-diketo-16R,S-fluoro-$PGE_1$ alkyl ester, 13,14-dihydro-15-keto-3R,S-methyl-$PGE_2$ alkyl ester, 13,14-dihydro-15-keto-16R,S-methyl-$PGE_2$ alkyl ester, 13,14-dihydro-6,15-keto-3R,S-16R,S-dimethyl-$PGE_2$ alkyl ester, 13,14-dihydro-16,16-dimethyl-$PGE_2$ alkyl ester, 13,14-dihydro-15-keto-16R,S-fluoro-$PGE_2$ alkyl ester, 13,14-dihydro-15-keto-19-methyl-$PGE_2$ alkyl ester.

Most preferable compounds are those having one or two lower alkyl group(s) such as methyl or ethyl groups(s) or hydroxyl group(s) on 16-position because of their excellent blood pressure increasing ability and cardiotonic action.

In the present specification PGEs are named based on a prostanoic acid skeleton, but it can be named according to IUPAC nomenclature, according to which, for instance, $PGE_1$, is nominated as 7-{(1R,2R,3R)-3-hydroxy-2-[(E)-(3S)-3-hydroxy-1-octenyl]-5-oxo-cyclopentyl}-heptanoic acid; $PGE_2$ is nominated as

(Z)-7-{(1R,2R,3R,)-3-hydroxy-2-[(E)-(3S)-3- hydroxy-1-octenyl]-5-oxo-cyclopentyl}-hept-5-enoic acid; 13,14-dihydro-15-keto-16R,S-fluoro-PGE$_2$ is nominated as (Z)7-{(1R,2R,3R)-3-hydroxy-2-[(4R,S)-4-fluoro-3-oxo-1-octyl]-5-oxo-cyclopentyl}-hept-5-enoic acid; 13,14-dihydro-15-keto20-ethyl-11-dehydroxy-11R-methyl PGE$_2$ methyl ester is nominated as Methyl (z)-7-{(1R,2S,3R)-3-methyl-2-[3-oxo-1-decyl]-5-oxo-cyclopentyl}-hept-5-enoate; and 13,14-dihydro6,15-diketo-19-methyl-PGE$_1$ ethyl ester is nominated as ethyl 7-{(1R,2R,3R)-3-hydroxy-2-(7-methyl-3-oxo-1-octyl)-5-oxocyclopentyl}-6-oxo-heptanoate.

The 15-keto-PGEs used in this invention may be prepared, for example, by the method noted in Japanese Patent Application No. 18326/1988. The disclosure on it is incorporated into a part of this specification.

A practical preparation of the 13,14-dihydro-15-keto PGEs involves the following steps; as shown in the synthetic charts (I) to (III), reaction of the aldehyde (2) prepared by the Collins oxidation of commercially available (−)-Corey lactone (1) with dimethyl (2-oxoheptyl)phosphate anion to give α,β-unsaturated ketone (3), reaction of the α,β- unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly generated hydroxy group with dihydropyrane to give the corresponding tetrahydropyranyl ether (7). According to the above process, a precursor of PGEs of which ω-chain is a 13,14-dihydro-15-keto-alkyl group is prepared.

A precursor of PGEs of which ω-chain is 15-ketoalkyl group can be obtained by proceeding the reaction without reduction of α,β-unsaturated ketons (3).

Using the above tetrahydropyranyl ether (7), 6-keto-PGE$_1$s (15) of which a group constituted with carbon atoms of 5-, 6- and 7-position is $$-CH_2-C(O)-CH_2-,$$

may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6- double bond and the hydroxyl group at 9-position with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms of 5-,6- and 7-position is

$$-CH_2-CH=CH-$$

may be prepared in the following steps; as shown in the synthetic chart II, reduction of the above the tetrahydropyranyl ether (7) to give the lactol (8), reaction of the resultant lactol (8) with the ylide generated from (4-carboxybutyl)triphenyl phosphonium bromide to give the carboxylic acid (16) followed by esterification to give ester (17), Jones oxidation of the esters (17) to give the compound (18), and removal of the protecting groups.

Using the above the tetrahydropyranyl ether (7) as starting material, the compound having

$$-CH_2-CH_2-CH_2-$$

may be prepared by using the same process for preparing PGE$_2$s having the group of

$$-CH_2-CH=CH-$$

and applying the resultant compound (18) to catalytic reduction for reducing the double bond between the 5- and 6-position followed by removal of the protection groups.

Synthesis of 5,6-dehydro-PGE$_2$s having $$-CH_2-C\equiv C-$$

may be carried out by alkylation of the resulting a copper enolate generated after 1,4-addition of a monoalkylcopper complex or a dialkylcopper complex of the following formula:

to 4R-t-butyldimethylsilyloxy-2-cyclopenten-1-one with 6-alkoxycarbonyl-1-iodo-2-hexyne or the derivatives.

The 11-β type PGEs can be prepared according to the synthetic chart III.

PGEs having a methyl group on 11-position instead of a hydroxyl group can be obtained by reacting PGAs with a dimethyl copper complex, which are prepared by Jones oxidation of a hydroxyl group on the 9-position of 11-tosylates. PGEs having a hydroxymethyl group on 11-position instead of a hydroxyl group can be prepared by photoaddition of methanol to the PGAs using benzophenone as a photosensitizer.

The 15-keto-PGEs of this invention may be used as a medicine for animals and human beings and usually applied systemically or locally by the method of oral administration, oral administration by spraying, intravenous injection (including instillation), subcutaneous injection, suppository and the like. Dose is determined depending on the animal to be treated the human patient, age, body weight, symptom, therapeutic effect, administration route, treating time and the like, but is preferably 0.001–500 mg/Kg.

As solid composition of this invention for oral administration, tablets, capsules, powders, granules and the like are included. The solid composition containing one or more active substances is mixed with at least an inactive diluent such as lactose, mannitol, glucose, hydroxypropyl cellulose, fine crystalline cellulose, starch, polyvinyl pyrolidone, magnesium aluminate metasilicate. The composition may contain except for the inactive diluent other additives such as lubricants (e.g. magnesium stearate), a disintegrator (e.g. cellulose calcium gluconate), a stabilizer (e.g. α-, β- or γ-cyclodextrin, etherated dextrin (e.g. dimethyl-α-, dimethyl-β-, trimethylβ- or hydroxypropyl-β-cyclodextrin), branched cyclodextrin (e.g. glucosyl- or maltosyl-cyclodextrin), formyl cyclodextrin, sulfur-containing cyclodextrin or misoprotol). Such cyclodextrins may form an inclusion compound with 15-keto-PGEs in some cases to increase the stability of the compounds. The stability may be often increased by forming lyposome with phospholipid. Tablets and pills may be coated with an enteric or gastroenteric film such as white sugar, gelatin, hydroxypropylcellulose, hydroxypropylmethylcellulose phthalate and the like, if necessary, and furthermore they may be covered with two or more layers. Additionally, the composition may be in the form of capsules made of substance easily absorbed such as gelatin.

Liquid compositions for oral administration include pharmaceutically acceptable emulsions, solutions, suspensions, syrups, elixirs and the like and contain a generally used inactive diluent such as purified water or ethyl alcohol. The composition may contain additives such as wetting agents and suspending agents as well as sweeteners, flavors, aromatics and preservatives.

The compositions for oral administration may contain one or more active substance.

The injection of this invention for non-oral administration includes sterile aqueous or nonaqueous solutions, suspensions, and emulsions. Diluents for the aqueous solution or suspension contain, for example, distilled water for injection, physiological saline and Ringer's solution.

Diluents for the nonaqueous solution and suspension contain, for example, propylene glycol, polyethylene glycol, vegetable oils such as olive oil, alcohols such as ethanol and polysorbates. The composition may contain other additives such as preservatives, wetting agents, emulsifying agents, dispersing agents and the like. These are sterilized by filtration through, e.g. a bacteria-preventing filter, compounding with a sterilizer, gas sterilization or radiation sterilization. These can be prepared by producing a sterile solid composition and dissolving it into sterilized water or a sterilized solvent for injection before use.

As a composition for intrarectal administration there may be included spherical or spindle shape medicines containing one or more active materials and one or more solid carriers such as cacaos or Carbowax, and a suppository such as gelatin capsules.

The present invention is illustrated by Examples in detail to clarify the effectiveness of the present invention. The term "effective components" used in the Examples means optional PGEs of the present invention.

EXAMPLE 1

(blood pressure, heart rate increasing action by intravenous injection)

Wister male rats (8 weeks old) were used as test animals.

The rats were applied to anesthesia by intraperitoneal administration with 1.25 g/kg of urethane. The blood pressure was determined by inserting a polyethylene tube into a femoral artery, which was connected with a pressure transducer. The heart rate was determined from R wave of electrocardiograms (ECG) induced by standard limb lead II with a tachometer. Each test compound was dissolved in ethanol and intravenously administered to rats in 1 mg/kg diluted with Ringer's solution just before use. The maximum concentration of ethanol was 2 percent. An ethanol-containing Ringer without any test compound was used as a control to confirm the influence of the ethanol in each experiment. Each changing rate (%) in the blood pressure and heart rate before and after administration was determined, and the average of 3–4 experiments was shown in Table 1.

TABLE 1

| test compound | changing rate of heart rate (%) | | | changing rate of blood pressure (%) | | |
|---|---|---|---|---|---|---|
| | 0.2 | 0.5 | 1 | 0.2 | 0.5 | 1 |
| 1* | 0 | 0 | +6 | 0 | 0 | −6 |
| 2 | +6 | +20 | +20 | 0 | +10 | +1 |
| 3 | | | +43 | | | +32 |
| 4 | +9 | +18 | +33 | +4 | +6 | +6 |
| 5* | 0 | 0 | 0 | 0 | 0 | −4 |
| 6 | +13 | +23 | +9 | +13 | +10 | +3 |
| 7 | +2 | +3 | +9 | +4 | +6 | +5 |
| 8 | +18 | +25 | +28 | +15 | +14 | +8 |
| 9 | 0 | +14 | +26 | 0 | 0 | +2 |
| 10 | +23 | +22 | +37 | +17 | +19 | +22 |
| 11 | +14 | +11 | +18 | +19 | +13 | +23 |
| 12 | +8 | +40 | +38 | +9 | +13 | +17 |
| 13 | +29 | +33 | +20 | +18 | +8 | +11 |
| 14 | +15 | +11 | +22 | +7 | +4 | +12 |
| 15 | +3 | +8 | +19 | +2 | +10 | +12 |
| 16 | | | +25 | | | +26 |
| 17 | | | +58 | | | +46 |
| 18 | +8 | +13 | +17 | +10 | +12 | +18 |
| 19 | | | +51 | | | +45 |
| 20* | 0 | 0 | 0 | 0 | 0 | −15 |
| 21 | +30 | +22 | +35 | +12 | +9 | +18 |
| 22 | 0 | +6 | +11 | 0 | 0 | +5 |
| 23 | 0 | 0 | +4 | 0 | 0 | +5 |
| 24 | 0 | 0 | +5 | 0 | 0 | +5 |
| 25 | 0 | 0 | +5 | 0 | 0 | +2 |
| 26 | 0 | 0 | +7 | 0 | 0 | +2 |
| 27 | +19 | +20 | +21 | +4 | +8 | +6 |
| 28 | +20 | +30 | +33 | +13 | +14 | +12 |
| 29 | +4 | +7 | +17 | +5 | +6 | +7 |
| 30 | +29 | +20 | +29 | +14 | +15 | +14 |
| 31 | +6 | +7 | +46 | +4 | +4 | +14 |
| 32 | +3 | +16 | +30 | +3 | +7 | +14 |
| 33 | +20 | +28 | +28 | +18 | +29 | +20 |
| 34 | 0 | +14 | +29 | 0 | +3 | +6 |
| 35 | +17 | +18 | +27 | +5 | +12 | +17 |
| 36 | | | +32 | | | +33 |
| 37 | | | +33 | | | +56 |
| 38 | +20 | +33 | +15 | +12 | +18 | +14 |
| 39 | | | +47 | | | +20 |
| 40 | +20 | +16 | +27 | +17 | +19 | +17 |
| 41 | +6 | +12 | +26 | +20 | +20 | +11 |
| 42 | 0 | 0 | +7 | 0 | 0 | +12 |
| 43 | +17 | +27 | +45 | +10 | +10 | +14 |
| 44 | +3 | +17 | +30 | +1 | +9 | +20 |
| 45 | 0 | 0 | +4 | 0 | 0 | +2 |
| 46 | 0 | 0 | +13 | 0 | 0 | +5 |
| 47 | 0 | 0 | +4 | 0 | 0 | +1 |
| 48 | | | +30 | | | +15 |
| 49 | 0 | 0 | +3 | 0 | 0 | +2 |
| 50 | 0 | 0 | +5 | 0 | 0 | +2 |
| 51 | 0 | 0 | +14 | 0 | 0 | +1 |
| 52 | | | 0 | | | +13 |
| 53 | | | +20 | | | +17 |
| 54 | | | +18 | | | +18 |
| 55 | | | +58 | | | +31 |
| 56* | +8 | +10 | +10 | −37 | −45 | −54 |
| 57* | +13 | +22 | +14 | −35 | −40 | −39 |
| 58* | +10 | +14 | +33 | −27 | −20 | −11 |
| 59* | | | 0 | | | 0 |

*(comparative example)

Test Compound

1: 13,14-dihydro-15-keto-PGE$_1$
2: 13,14-dihydro-15-keto-PGE$_1$ ethyl ester
3: 13,14-dihydro-15-keto-$\Delta^2$-PGE$_1$ methyl ester 4: 13,14-dihydro-15-keto-20-ethyl-PGE$_1$ methy ester
5: 13,14-dihydro-6,15-diketo-PGE$_1$
6: 13,14-dihydro-6,15-diketo-PGE$_1$ methyl ester
7: 13,14-dihydro-6,15-diketo-PGE$_1$ ethyl ester
8: ($\pm$) 13,14-dihydro-6,15-diketo-PGE$_1$ ethyl ester
9: 13,14-dihydro-6,15-diketo-PGE$_1$ n-butyl ester
10: 13,14-dihydro-6,15-diketo-16R,S-methyl-PGE$_1$ methyl ester
11: 13,14-dihydro-6,15-diketo-16R,S-methyl-PGE$_1$ ethyl ester
12: 13,14-dihydro-6,15-diketo-16,16-dimethyl-PGE$_1$ ethyl ester
13: 13,14-dihydro-6,15-diketo-16R,S-fluoro-PGE$_1$ ethyl ester,
14: 13,14-dihydro-6,15-diketo-19-methyl-PGE$_1$ methyl ester
15: 13,14-dihydro-6,15-diketo-19-methyl-PGE$_1$ ethyl ester
16: 13,14-dihydro-6,15-diketo-11-dehydroxy-11R-hydroxymethyl-19-methyl-PGE$_1$ methyl ester
17: 13,14-dihydro-6,15-diketo-11-dehydroxy-11R-methyl-PGE$_1$ methyl ester
18: 13,14-dihydro-6,15-diketo-11-dehydroxy-11R-methyl-PGE$_1$ ethyl ester
19: 13,14-dihydro-6,15-diketo-16R,S-fluoro-11R-dehydroxy-11R-methyl-PGE$_1$ ethyl ester
20: 13,14-dihydro-15-keto-PGE$_2$
21: 13,14-dihydro-15-keto-PGE$_2$ methyl ester
22: 13,14-dihydro-15-keto-PGE$_2$ ethyl ester
23: 13,14-dihydro-15-keto-PGE$_2$ n-propyl ester
24: 13,14-dihydro-15-keto-PGE$_2$ n-butyl ester
25: 13,14-dihydro-15-keto-PGE$_2$ benzyl ester
26: 13,14-dihydro-15-keto-PGE$_2$ hydroxyethyl ester
27: 13,14-dihydro-15-keto-$\Delta^2$-PGE$_2$-methyl ester
28: 13,14-dihydro-15-keto-3R,S-methyl-PGE$_2$ methyl ester
29: 13,14-dihydro-15-keto-3R,S-methyl-PGE$_2$ ethyl ester
30: 13,14-dihydro-15-keto-16R,S-methyl-PGE$_2$ methyl ester
31: 13,14-dihydro-15-keto-16R,S-methyl-PGE$_2$ ethyl ester
32: 13,14-dihydro-15-keto-3R,S-16R,S-dimethyl-PGE$_2$ methyl ester
33: 13,14-dihydro-15-keto-16,16-dimethyl-PGE$_2$ methyl ester
34: 13,14-dihydro-15-keto-16,16-dimethyl-PGE$_2$ ethyl ester
35: 13,14-dihydro-15-keto-16R,S-hydroxy-PGE$_2$ ethyl ester
36: 13,14-dihydro-15-keto-16R,S-fluoro-PGE$_2$ (tautomericisomer between carbonyl group at carbon atom of 15-position and hydroxyl group on carbon atom of 11-position is confirmed.)
37: 13,14-dihydro-15-keto-16R,S-fluoro-PGE$_2$ methyl ester
38: 13,14-dihydro-15-keto-16R,S-fluoro-PGE$_2$ ethyl ester
39: 13,14-dihydro-15-keto-16R,S-fluoro-20-methylPGE$_2$ methyl ester
40: 13,14-dihydro-15-keto-16R,S-fluoro-11-dehydroxy-11R-methyl-PGE$_2$ ethyl ester
41: 13,14-dihydro-15-keto-11-dehydroxy-11R-methylPGE$_2$ ethyl ester
42: 13,14-dihydro-15-keto-17S-methyl-PGE$_2$ methyl ester
43: 13,14-dihydro-15-keto-19-methyl-PGE$_2$ methyl ester
44: 13,14-dihydro-15-keto-19-methyl-PGE$_2$ ethyl ester
45: 13,14-dihydro-15-keto-20-methoxy-PGE$_2$ methyl ester
46: 13,14-dihydro-15-keto-20-methoxy-$\Delta^2$-PGE$_2$ methyl ester
47: 13,14-dihydro-15-keto-3R,S-methyl-20-methoxy-PGE$_2$ methyl ester
48: 13,14-dihydro-15-keto-16,16-dimethyl-20-methoxy-PGE$_2$ methyl ester
49: 13,14-dihydro-15-keto-20-isopropylidene-PGE$_2$
50: 13,14-dihydro-15-keto-20-isopropylidene-PGE$_2$ methyl ester
51: 13,14-dihydro-15-keto-20-ethyl-PGE$_2$ methyl ester
52: 13,14-dihydro-15-keto-20-ethyl-PGE$_2$ ethyl ester
53: 13,14-dihydro-15-keto-20-ethyl-11-dehydroxy-11R-methyl-PGE$_2$ methyl ester
54: 13,14-dihydro-15-keto-20-n-propyl-PGE$_2$ methyl ester
55: 15-keto-16R,S-fluoro-PGE$_2$ methyl ester
56: PGE$_1$
57: PGE$_2$
58: PGE$_2$ methyl ester
59: control The test compound (esters of 15-keto-PGEs) exhibits a blood pressure increasing effect instead of showing a blood pressure decreasing effect which are observed in PGs such as PGE$_2$, PGE$_2$ methyl esters; and 15-keto-PGEs having a free carboxylic acid residue such as 13,14-dihydro-15-ketoPGE$_2$. The esters of 15-keto-PGEs also exhibits positive chronotropic effect (cardiotonic effect).

EXAMPLE 2

Changing rates of blood pressure and heart rate were determined in the same manner as described in Example 1 except that the test compounds 60, 61 and 62 were used in different concentrations instead of the test compounds 1-55. The results were shown in Table 2.

TABLE 2

| test compound | dose mg/kg | changing rate (%) of blood pressure | changing rate (%) of heart rate |
|---|---|---|---|
| 60 | 0.1 | +17 | +14 |
|  | 1 | +13 | +38 |
| 61 | 0.01 | +13 | +14 |
|  | 0.1 | +15 | +30 |
|  | 1 | +27 | +26 |
| 62 | 0.1 | — | +6 |
|  | 1 | — | +13 |

Test Compound 60. 13,14-dihydro-15-keto-20-methyl-PGE$_1$ methyl ester
61. 13,14-dihydro-15-keto-16,16-difluoro-PGE$_2$ methyl ester
62. 13,14-dihydro-6,15-diketo-18-methyl-PGE$_1$ ethyl ester

EXAMPLE 3

Wister male rats (9 weeks old) were used.
The rats were applied to anesthesia by intraperitoneal administration with 1.25 g/kg of urethane. The blood flow rate in carotid was determined by a stromuhr. The blood pressure and heart rate were determined according to the same manner as in Example 1.

Figure 1A:
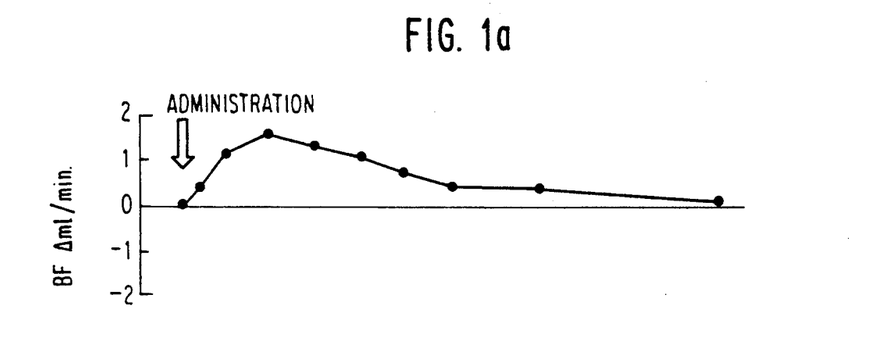
FIG. 1a, 1b and 1c are graphs showing an effect of 13,14-dihydro-6,15-diketo-19-methyl-$PGE_1$ ethyl ester on blood flow rate (BF) (FIG. 1a), blood pressure (BP) (FIG. 1b) and heart rate (HR) (FIG. 1c)
Figure 1B:
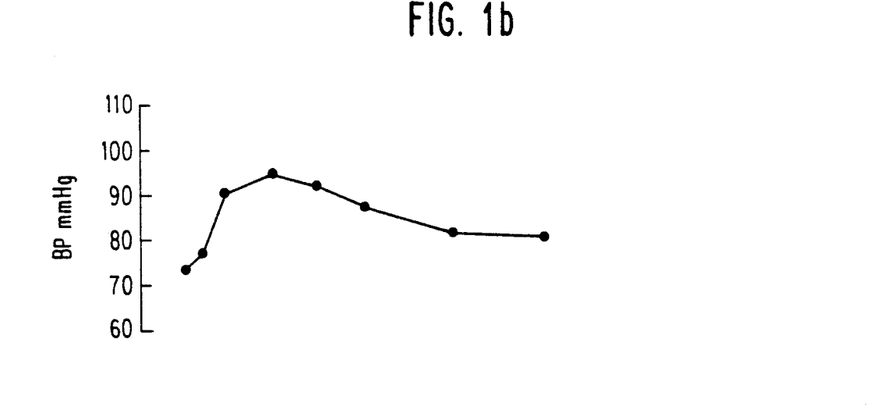
Figure 1C:
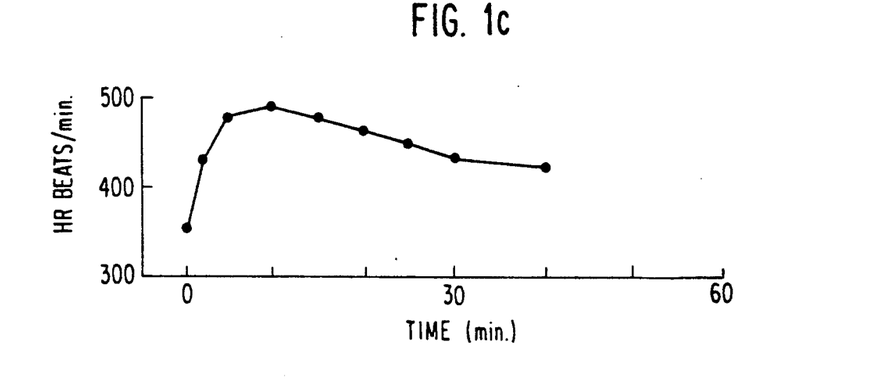

13,14-dihydro-6,15-diketo-19-methyl-PGE$_1$ ethyl ester (sample number: 15) was dissolved in a small amount of ethanol, and then diluted with Ringer's solution more than 50 times. About 0.1 ml (1 mg drag/kg rat) of the diluted solution was administered to a rat through a polyethylene tube inserted into a femoral artery. The changes in blood flow rate (BF), blood pressure (BP), heart rate (HR) were observed, and the average of 4 experiments were shown in FIG. 1.

Apparent from FIG. 1 BF, BP and HR extremely increase.

EXAMPLE 4

(Recovery of blood pressure and heart rate of rats in hemorrhage shock)

Wister male rats (8 weeks old) were applied to anesthesia by subcutaneous injection with 1.5 g/kg of urethane. The blood pressure and heart rate were determined according to the same manner as in Example 1.

The rats were kept for 60 minutes in a room after a blood corresponding to 1.5% of the weight was removed.

13,14-dihydro-6,15-diketo-19-methyl-PGE$_1$ ethyl ester (compound number 15) was dissolved in Ringer's solution (0.1 ml), and the solution was intravenously administered into the above dehematized rat. Ringer's solution was administered to a control group.

The recovery rates of the blood pressure and heart rate were obtained assuming the value at 60 minutes after dehematizing being 0% and the value before dehematizing being 100% respectively. The average value of 5 experiments was shown in Table 3. Typical change of blood pressure with time was shown in FIG. 2, and heart rate change with time was shown in FIG. 3. In these FIGS. (1), (2) and (3) represent a dose of 1 mg/kg, dose of 0.5 mg/kg and control respectively.

The same procedure as the above except that the compounds of (7), (18) and (22) were used instead of the compound (15) was applied, and the effects are observed, the results of which are also shown in Table 3.

Figure 2:
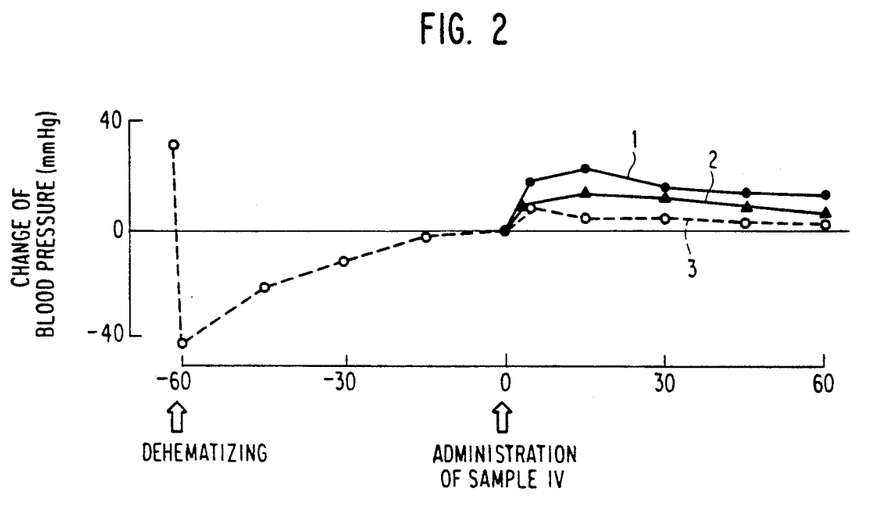
FIGS. 2 and 3 are graphs showing an effect of 13,14-dihydro-6,15-diketo-19-methyl-$PGE_1$ ethyl ester on recovery of low blood pressure when dehematized, and on recovery of heart rate respectively.
Figure 3:
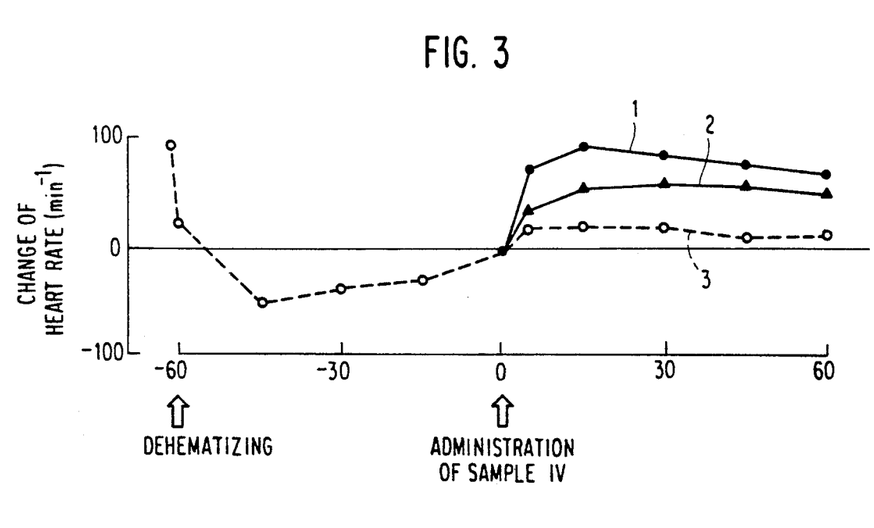

Apparent from Table 3 and FIGS. 2 and 3 a remarkable recovering of the blood pressure and heart rate by the administration of the test compounds was observed.

TABLE 3

| test compound | dose mg/kg | recovering of blood pressure % | recovering of heart rate % |
| --- | --- | --- | --- |
| 7 | 0.5 | 38 | 46 |
|   | 1.0 | 63 | 62 |
| 15 | 0.5 | 39 | 62 |
|   | 1.0 | 68 | 100 |
| 18 | 0.5 | 87 | 100 |
|   | 1.0 | 119 | 100 |
| 22 | 0.5 | 32 | 50 |
|   | 1.0 | 74 | 63 |

EXAMPLE 5

Acute toxicity LD$_{50}$ of 15-keto-PGE esters to Sleddy mice was determined at oral administration (PO), subcutaneous administration (SC), intraperitoneally administration (I.P.), or intravenous administration (IV). The results were shown in Table 4.

TABLE 4

| test compound | administration | LD$_{50}$ (mg/kg) male | female |
| --- | --- | --- | --- |
| 22 | PO | >4000 | >4000 |
|   | SC | >1000 | >1000 |
|   | IP | >500 | >500 |
|   | IV | 1000 | 1000 |
| 21 | IV | >1000 |   |
| 2 | IP | >1000 |   |
|   | IV | >1000 |   |
| 15 | IV | >300 |   |
| 36 | PO | >500 |   |
| 37 | PO | >500 |   |

EXAMPLE 6

(progressing a breath)

Wister male rats (8 weeks old) were applied to anesthesia by intraperitoneal administration with 1.25 g/kg of urethane. A pick-up for breath was fixed on a top of a rat's nose, and the breath curve was recorded on a polygraph while the breath rate was counted with a tachometer.

Each test compound was dissolved in ethanol and administered to rats through a tale vein in 1 mg/kg as diluted with Ringer's solution just before use. The maximum concentration of ethanol was 2 percent. Ringers solution containing ethanol but not containing test compound was administered at every experiment as a control. The change rates (%) of the breath rate before and after administration were determined, and evaluated as progressing activity of breath. The results were shown in Table 5.

EXAMPLE 7

(enteroconstriction)

Ileums were enuculated from Wister male rats, and hung up in Magnus tube. The ileums were administered with test compounds, after they were constricted several times by immersed into an acetylcholine solution of $1 \times 10^{-6}$ g/ml and two constrictions were observed at the same level.

The ileum constrictions by the test compounds were evaluated by the concentration of a test compound exhibiting 50% of the constriction achieved by the acetylcholine solution of $1 \times 10^{-6}$ g/ml. This concentration was expressed by ED$_{50}$. The results were shown in Table 5.

TABLE 5

| test compound | progressing activity % of breath* | enteroconstriction** |
| --- | --- | --- |
| 1 | +34 |   |
| 2 | +47 |   |
| 4 | +48 |   |
| 5 | +4 |   |
| 6 | +21 | — |
| 7 | +31 |   |
| 8 | +65 |   |
| 9 | +26 | — |
| 10 | +63 |   |
| 11 | +34 | — |
| 12 | +44 | — |
| 13 | +53 |   |
| 14 | +33 |   |
| 15 | +26 | — |
| 18 | +28 | — |
| 20 | +12 |   |
| 21 | +29 | — |
| 22 | +28 | — |
| 23 | +37 | — |
| 24 | +41 |   |
| 25 | +22 | — |

TABLE 5-continued

| test compound | progressing activity % of breath* | enterocon- striction** |
|---|---|---|
| 26 | +22 | — |
| 27 | +11 | — |
| 28 | +40 | — |
| 29 | +11 | — |
| 30 | +61 | — |
| 31 | +40 | |
| 32 | +41 | — |
| 33 | +40 | — |
| 34 | +31 | — |
| 35 | +37 | — |
| 38 | +47 | — |
| 40 | +16 | |
| 41 | +20 | |
| 42 | +28 | — |
| 43 | +41 | |
| 44 | +16 | — |
| 45 | +10 | — |
| 46 | +10 | — |
| 47 | +17 | — |
| 49 | +18 | — |
| 50 | +18 | — |
| 51 | +49 | — |
| 57 | +55 | + |
| 58 | +35 | |
| 59 | 0 | — | note:
*—: exhibiting the progressing activity of breath
**—: $ED_{50} \geq 10^{-6}$
+: $ED_{50} < 10^{-6}$
slanted lines show not tested.

As apparent from the above results PGEs have progressing activity of breath in general, and 15-keto-PGEs and 13,14-dihydro-15-keto-PGEs have no enteroconstricting action as a side effect.

EXAMPLE 8

(preparation of capsules)

One or more effective compound 50 mg was dissolved in ethanol (10 ml), and the solution was mixed with mannitol 18.5 g to give a wet mass. The wet mass was sifted through a 30-mesh sieve, the mass passed was dried at 30° C. for 90 minutes, and then sifted through the 30-mesh sieve again. The obtained powder was added with a microfine silica (Aerosil) 200 g and mixed. The mixed powder was filled into 100 hard gelatine capsules (No. 3) to give capsules containing 0.5 mg of the effective compound a capsule, which were soluble in the intestines.

EXAMPLE 9

(preparation of a powder for injection)
Following ingredients were mixed:

| ingredients | parts by weight |
|---|---|
| effective compounds | 1 |
| Tween 80* | 0.1 |
| mannitol | 5 |
| distilled water | 0.4 |

*sorbitan mono oleyl ester condensed with ethyleneoxide (20 mole).

The mixture was sterilized, filtrated and then freeze-dried to give a powder for injection.

EXAMPLE 10

(preparation of a liquid for injection)
Following ingredients were mixed, and sterilized to give a liquid for injection.

| ingredients: | parts by weight |
|---|---|
| effective compounds | 0.2 |
| nonionic surface active agents | 2 |
| distilled water for injection | 98 |

EXAMPLE 11

(preparation of a powder for oral administration)
Following ingredients were mixed to give a powder for oral administration.

| ingredients: | parts by weight |
|---|---|
| effective compounds | 5 |
| light dry silicic acid | 5 |
| Abicel | 20 |
| lactose | 70 |

EXAMPLE 12

(preparation of a soft capsule)
Following ingredients were mixed and filled up into a soft capsule.

| ingredients | parts by weight |
|---|---|
| effective compounds | 1 |
| Pasenat | 999 |

Synthetic Chart I

-continued
Synthetic Chart I

-continued
Synthetic Chart I (14)

(15)

Synthetic Chart II (7)

(8)

(16)

-continued
Synthetic Chart II (17)

(18)

(19)

Synthetic Chart III (22)

(23)

(24)

-continued
Synthetic Chart III

What is claimed is:

1. A method for causing hypersphyxia by increasing at least one of blood pressure, heart rate, blood flow rate and hyperventilation in a subject in need thereof suffering from hypergasia of the circulation, which method comprises administering to the subject an effective amount of a 15-keto-PGE ester.

2. A method of the claim 1, wherein the hypergasia is hypertension, decrease in heart rate or decrease in blood pressure.

3. A method of the claim 1, wherein the 15-keto-PGE ester is of the formula:

wherein $R_1$ is a hydroxyl group, a hydroxyalkyl group, or an alkyl group; Y is a saturated or an unsaturated hydrocarbon moiety having 2-6 carbon atoms wherein a portion of carbon atoms constituting the hydrocarbon moiety may be carbonyl or hydrocarbon moiety may be substituted with other atoms or groups; Z is a saturated or an unsaturated hydrocarbon moiety having 1-10 carbon atoms which may constitute a ring or the hydrocarbon moiety may be substituted with other atoms or groups; $COOR_2$ wherein $R_2$ is a saturated or unsaturated lower alkyl, cycloalkyl of 3 to 6 carbon atoms, substituted or unsubstituted phenyl or benyzl, hydroxyalkyl, alkoxyalkyl, trialkysilyl or tetrahydropyranyl, is a physiologically acceptable ester group thereof.

4. A method of the claim 3, wherein Z represents a formula:

—$CH_2CH_2CH_2CH(R_1)(R_2)$:

wherein $R_1$ is a hydrogen atom or a methyl group, and $R_2$ is a methyl group, an ethyl group or a propyl group.

5. A method of the claim 3, wherein Z is a fluoroalkyl group.

6. A method of the claim 1, wherein the hydrocarbon moiety represented by Z is substituted with one or more group(s) or atom(s) selected from the group consisting of a hydroxyl group, an alkyl group, a phenyl group, an alkoxy group and a phenoxy group or a halogen atom.

7. A method of the claim 1, wherein 15-keto-PGE ester is a 6,15-diketo-PGE ester.

8. A method of the claim 1, wherein 15-keto-PGE ester is a 15-keto-3-alkyl-PGE ester.

9. A method of said claim 1, wherein said 15-keto-PG ester is selected from the group consisting of a 15-keto-16-monoalkyl-PGE ester and a 15-keto-16-dialkyl-PGE ester.

10. A method of the claim 1, wherein said 15-keto-PG ester is selected from the group consisting of a 15-keto-16-monohalogen-PGE ester and a 15-keto-16-dihalogen-PGE ester.

11. A method of the claim 1, wherein 15-keto-PGE ester is a 15-keto-19-alkyl-PGE ester.

12. A method of the claim 1, wherein 15-keto-PGE ester is a 15-keto-20-alkyl-PGE ester.

13. A method of the claim 1, wherein the effective amount is 0.001–500 mg/kg.

14. A method of the claim 1, wherein 15-keto-PGE ester is a 13,14-dihydro-15-keto-PGE ester.

15. A method of the claim 1, wherein said causing of hypersphyxia is by increasing heart rate and blood pressure.

16. A method for causing an increase in blood pressure of a subject in need thereof suffering from hypergasia of the circulation, which method comprises administering to said subject an effective amount of a 15-keto-PGE ester.

17. A method for increasing a heart rate in a subject in need thereof suffering from hypergasia of the circulation, which method comprises administering to said subject an effective amount of a 15-keto-PGE ester.

18. A method for increasing a breath rate of a subject in need thereof suffering from hypergasia of the circulation, which method comprises administering to said subject an effective amount of a 15-keto-PGE ester.

19. A method for increasing a blood flow rate in a subject in need thereof suffering from hypergasia of the circulation, which circulation, which method comprises administering to the subject an effective amount of a 13,14-dihydro-15-keto-PGE ester.

* * * * *